United States Patent
Hirayama

(10) Patent No.: US 8,596,792 B2
(45) Date of Patent: Dec. 3, 2013

(54) OPTOTYPE PRESENTING APPARATUS

(75) Inventor: Yukito Hirayama, Aichi (JP)

(73) Assignee: Nidek Co., Ltd., Aichi (JP)

(*) Notice: Subject to any disclaimer, the term of this patent is extended or adjusted under 35 U.S.C. 154(b) by 6 days.

(21) Appl. No.: 13/273,424

(22) Filed: Oct. 14, 2011

(65) Prior Publication Data

US 2012/0092622 A1   Apr. 19, 2012

(30) Foreign Application Priority Data

Oct. 15, 2010  (JP) ................................ 2010-232935

(51) Int. Cl.
*A61B 3/02* (2006.01)
*A61B 3/032* (2006.01)

(52) U.S. Cl.
CPC ...................................... *A61B 3/032* (2013.01)
USPC ........................................................ 351/240

(58) Field of Classification Search
USPC ......... 351/200–204, 222–223, 227, 230–232, 351/237, 239, 243
See application file for complete search history.

(56) References Cited

U.S. PATENT DOCUMENTS 7,404,639 B2 * 7/2008 Nishihira et al. ............. 351/203
2005/0264760 A1   12/2005 Ikezawa

FOREIGN PATENT DOCUMENTS

EP        2095760 A1 *  9/2009
EP        2095760 B1     5/2011
JP        2009-207569 A  9/2009

* cited by examiner

*Primary Examiner* — Scott J Sugarman
*Assistant Examiner* — Robert E Tallman
(74) *Attorney, Agent, or Firm* — Lowe Hauptman & Ham LLP

(57) ABSTRACT

An optotype presenting apparatus for presenting an optotype used to test a visual function of an examinee includes: an optotype presentation part configured to present the optotype in a predetermined presentation region; a control unit configured to allow a test optotype to be presented in the optotype presentation part, the test optotype including a stereoscopic vision test optotype that generates a parallax so as to be seen by the examinee as floating or sinking from a predetermined reference plane; and an optotype splitting unit configured to split the test optotype presented in the optotype presentation part into an optotype for a left eye and an optotype for a right eye to present the test optotype to right and left eyes of the examinee, wherein the test optotype includes a guide optotype for guiding the examinee to see the stereoscopic vision test optotype stereoscopically.

13 Claims, 7 Drawing Sheets

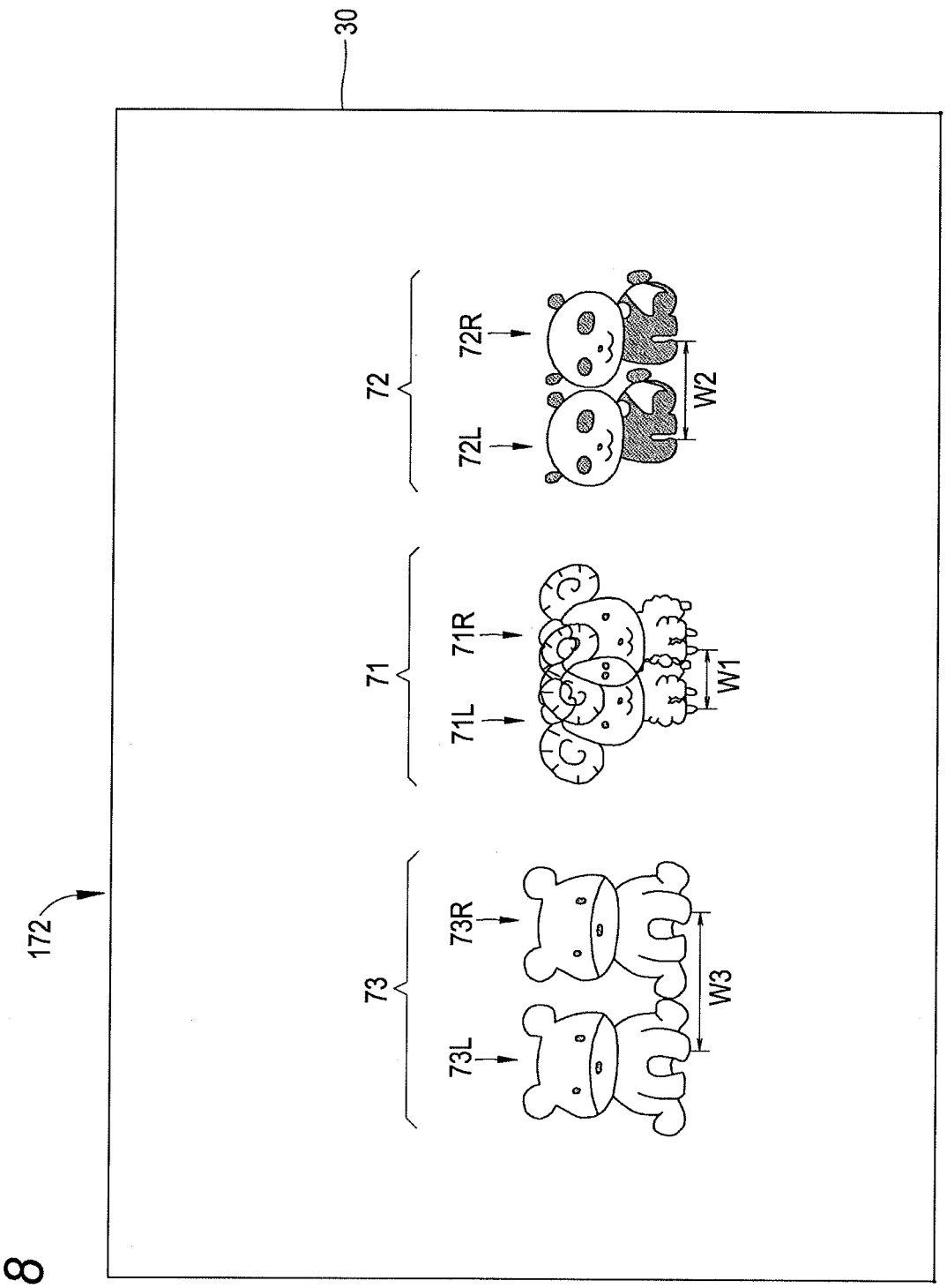

OPTOTYPE PRESENTING APPARATUS

CROSS-REFERENCE TO RELATED APPLICATION

This application is based on Japanese Patent Application No. 2010-232935 filed with the Japan Patent Office on Oct. 15, 2010, the entire content of which is hereby incorporated by reference.

BACKGROUND

1. Technical Field

The present disclosure relates to an optotype presenting apparatus for presenting an optotype used for a visual function test to an examinee.

2. Related Art

In recent years, optotype presenting apparatuses for testing visual functions including a visual acuity of eyes of an examinee have been known. Such an optotype presenting apparatus presents (displays) various optotypes on a display such as a liquid crystal panel (e.g., see JP-A-2009-207569). The optotype presenting apparatus presents an optotype that generates a parallax to right and left eyes of an examinee, for example, by the use of polarization so that a binocular vision test such as a stereoscopic vision test can be performed.

In a stereoscopic vision test, an optotype for a left eye is presented to the left eye of an examinee, whereas an optotype for a right eye is presented to the right eye of the examinee. The examinee fuses both optotypes presented to the right and left eyes, and the optotype appears to float (or sink). Accordingly, a stereoscopic vision function of the examinee is tested by determining the degree of floating (or sinking) of the optotype seen by the examinee and how the optotype is seen by the examinee, for example.

SUMMARY

An optotype presenting apparatus for presenting an optotype used to test a visual function of an examinee includes: an optotype presentation part configured to present the optotype in a predetermined presentation region; a control unit configured to allow a test optotype to be presented in the optotype presentation part, the test optotype including a stereoscopic vision test optotype that generates a parallax so as to be seen by the examinee as floating or sinking from a predetermined reference plane; and an optotype splitting unit configured to split the test optotype presented in the optotype presentation part into an optotype for a left eye and an optotype for a right eye to present the test optotype to right and left eyes of the examinee, wherein the test optotype includes a guide optotype for guiding the examinee to see the stereoscopic vision test optotype stereoscopically, and the guide optotype generates a parallax so that the guide optotype is seen by the examinee as floating or sinking from the reference plane continuously or stepwise.

BRIEF DESCRIPTION OF THE DRAWINGS

FIG. 8 is a diagram illustrating the optotype image after a certain time period has elapsed from the initial state.

DESCRIPTION OF EMBODIMENTS

Figure 1:
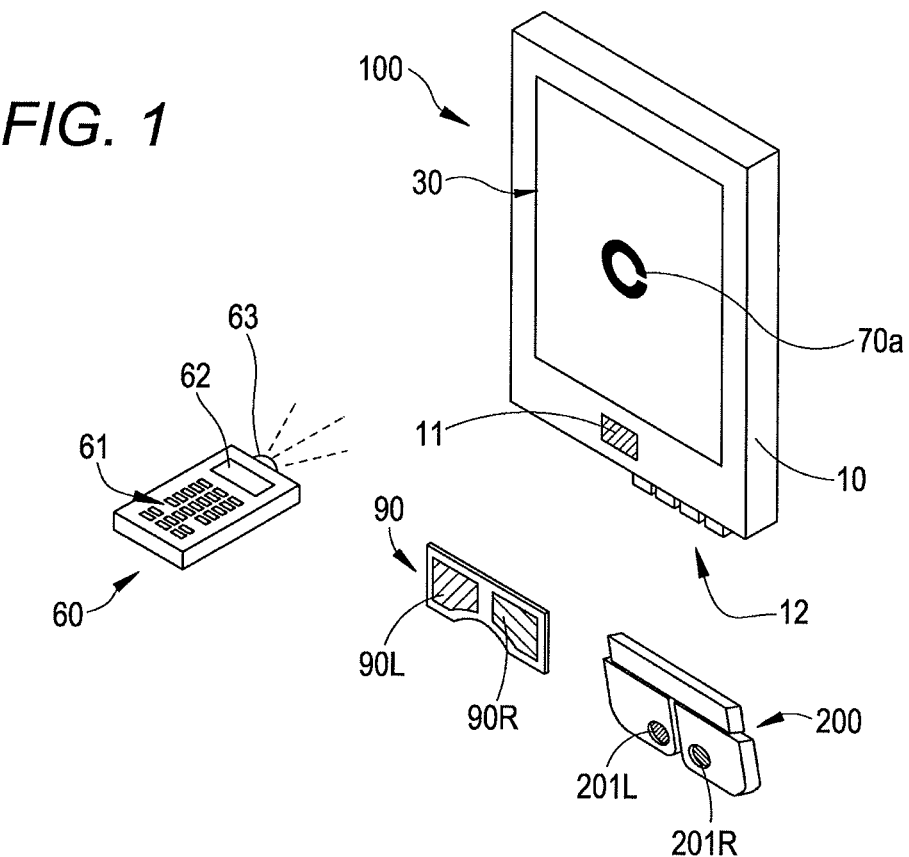
FIG. 1 is a schematic outline drawing of an optotype presenting apparatus according to a first embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

There are cases where examinees who are not accustomed to a stereoscopic vision test cannot stereoscopically see an optotype in spite of having normal stereoscopic vision functions. For example, such an examinee may see an optotype for a left eye and an optotype for a right eye independently (not fusing well). Specifically, examinees (e.g., small children) who have difficulty understanding the meaning of the stereoscopic vision test cannot readily see the optotype in a stereoscopic manner. In such cases, test efficiency is markedly deteriorated.

A technical object of the present disclosure is to provide an optotype presenting apparatus capable of efficiently conducting a binocular vision test such as a stereoscopic vision test by allowing an examinee to readily see an optotype in a stereoscopic manner.

Now, an optotype presenting apparatus according to a first embodiment is described with reference to the drawings. FIG. 1 is a schematic outline drawing of an optotype presenting apparatus 100 according to the first embodiment. The optotype presenting apparatus 100 includes an optotype presentation part (optotype presentation means or optotype presentation unit) 30 arranged in a front surface of a housing 10. The optotype presentation part 30 includes a screen (predetermined presentation region). The screen has a size large enough to present (display) an optotype such as a visual acuity test optotype 70a (e.g., Landolt ring for visual acuity of 2.0) having a predetermined size to an examinee even when the optotype presentation part 30 is positioned at a distance of, for example, 5 meters away from the examinee. The optotype presentation part 30 has a color liquid crystal display 31 serving as a presentation unit (display means or display unit) arranged inside thereof (see FIG. 2).

A receiving portion 11 serving as a receiving unit (receiving means) is arranged in a lower portion of the front surface of the housing 10. The receiving portion 11 receives infrared light (light signal) from a remote control 60 serving as an operation unit (operation means). Function keys (buttons) 12 are also arranged on the lower portion of the housing 10. These function keys 12 serves as a setting unit (input unit or input (setting) means) used for various settings (inputs) of the optotype presenting apparatus 100.

The optotype presenting apparatus 100 has the remote control 60. The remote control 60 includes a plurality of keys (buttons) 61, a liquid crystal display 62, and a transmitting portion 63. The keys 61 serve as an optotype selection unit (optotype selection means) used to select an optotype to be displayed on the display 31. The liquid crystal display 62 serves as a display unit (display means) for displaying a selected optotype, for example. The liquid crystal display 62 may be a monochrome display or a color display. The transmitting portion 63 serves as a transmitting unit (transmitting means) for transmitting infrared light (light signal).

Figure 2:
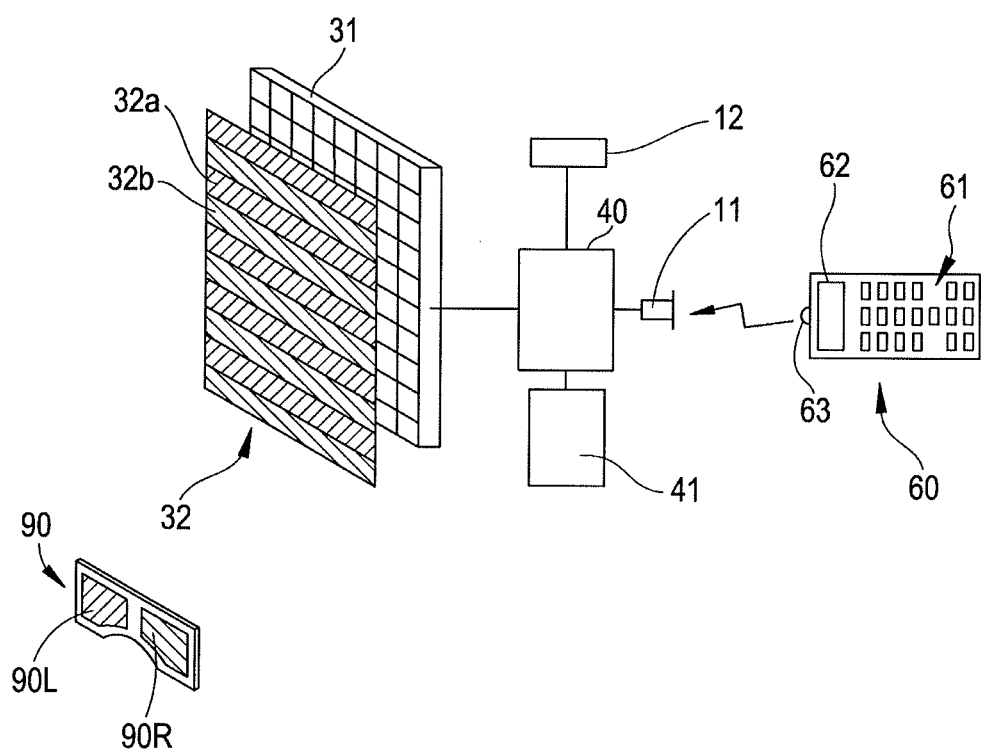
FIG. 2 is a schematic block diagram illustrating an optotype presentation part and a control system of the optotype presenting apparatus.

FIG. 2 is a schematic block diagram illustrating the optotype presentation part 30 and a control system of the optotype presenting apparatus 100. The optotype presentation part 30 includes the display 31 and a polarizing optical member 32. The polarizing optical member 32 is arranged (attached) in a front surface of the display 31 and is shaped in a sheet. The polarizing optical member 32 has a size that covers at least an optotype presentation (display) region of the display 31.

The display 31, the receiving portion 11, and the function keys 12 are connected to a control unit 40. The control unit (control means) 40 controls the optotype presenting apparatus 100. The control unit 40 is connected with a memory 41. The memory 41 serves as a storage unit (storage means) for storing various optotypes. The control unit 40 includes a decoder circuit for decoding a command signal from the remote control 60. The control unit 40 controls display of each pixel of the display 31 by, for example, an optotype switching command signal that is input from the remote control 60 (i.e., optotype is displayed on display 31).

A structure of the polarizing optical member 32 is now described. The display 31 emits linearly polarized light. The linearly polarized light has a polarizing axis that is directed toward a predetermined direction (vertical direction, horizontal direction, or direction inclined at an angle of 45 degrees). In this embodiment, the linearly polarized light having the polarizing axis in a vertical direction is emitted. The polarizing optical member 32 includes optical regions 32a and 32b each of which has a line shape. The optical regions 32a and 32b extend in a lateral direction (horizontal direction) for the size of pixels of the display 31. The optical regions 32a and 32b are arranged alternately in a longitudinal direction (vertical direction), and allow the light emitted from the display 31 to pass therethrough to convert the light into linearly polarized light. A polarizing axis of the linear polarized light resulting from passing through the optical region 32a and a polarizing axis of the linear polarized light resulting from passing through the optical region 32b are perpendicular to each other. The polarizing optical member 32 has a phase difference function that is substantially equal to that of a half-wave plate. As is commonly known, the half-wave plate rotates a vibration direction of incident light by 2×θ. The symbol θ represents an angle formed by a polarizing axis of the incident light and a fast axis (slow axis) of the half-wave plate. That is, the half-wave plate has a function of rotating a polarizing axis direction (vibration direction) of incident light by inclination of the polarizing axis direction of the incident light so as to be coincident with an optical principal axis direction serving as a fast axis (slow axis) of the half-wave plate. The half-wave plate has a function of maintaining quantity of the incident light as it is.

In a binocular vision test including a stereoscopic vision test, an examinee wears a pair of polarized glasses 90. The pair of polarized glasses 90 includes polarizing filters 90L and 90R that have polarizing axes perpendicular to each other. The polarizing filter 90L is placed in front of a left eye of the examinee, whereas the polarizing filter 90R is placed in front of a right eye of the examinee. In this embodiment, the polarizing filter 90L has the polarizing axis oriented in a 45-degree direction. The polarizing filter 90R has the polarizing axis oriented in a 135-degree direction. A subjective refractometer (hereinafter called phoropter) 200 may be used instead of the pair of polarized glasses 90. The phoropter 200 has right and left test windows in which a spherical lens, a cylindrical lens, an attachment lens, and other lenses are placed and switched with another. When the phoropter 200 is used, polarizing filters 201L and 201R are placed on the left test window and the right test window, respectively. The polarizing filters 201L and 201R have polarizing axes that are perpendicular to each other.

The optical region 32a of the polarizing optical member 32 serves as an optical region for a left eye. In this embodiment, the optical region 32a has an optical principal axis direction that is arranged such that a polarizing axis direction of the light emitted from the display 31 is coincident with a polarizing axis direction (45-degree direction) of the polarizing filter 90L (or polarizing filter 201L) for the left eye of the polarized glasses 90 (or phoropter 200). The optical region 32b serves as an optical region for a right eye. In this embodiment, the optical region 32b has an optical principal axis direction that is arranged such that a polarizing axis direction of the light emitted from the display 31 is coincident with a polarizing axis direction (135-degree direction) of the polarizing filter 90R (or polarizing filter 201R) for the right eye of the polarized glasses 90 (or phoropter 200). Therefore, when the examinee sees the optotype presentation part 30 through the polarizing filters 90L and 90R (or polarizing filters 201L and 201R) arranged in front of right and left eyes thereof, the left eye recognizes the light from the optical region 32a that is capable of passing through the polarizing filter 90L (or polarizing filter 201L). On the other hand, the light from the optical region 32b is blocked by the polarizing filter 90L (or polarizing filter 201L) and is not recognized by the left eye. The right eye recognizes the light from the optical region 32b that is capable of passing through the polarizing filter 90R (or polarizing filter 201R). On the other hand, the light from the optical region 32a is blocked by the polarizing filter 90R (or polarizing filter 201R) and is not recognized by the right eye. Accordingly, the light from the display 31 is split and entered into the right and left eyes of the examinee, so that different optotypes are presented to the right and left eyes of the examinee. That is, optotypes generating a parallax (optotypes for stereoscopic vision test) are presented to the right and left eyes of the examinee. Thus, the polarizing optical member 32 and the pair of polarized glasses 90 (or phoropter 200) function as a splitting unit for splitting the optotype presented (displayed) on the display 31.

Figure 3:
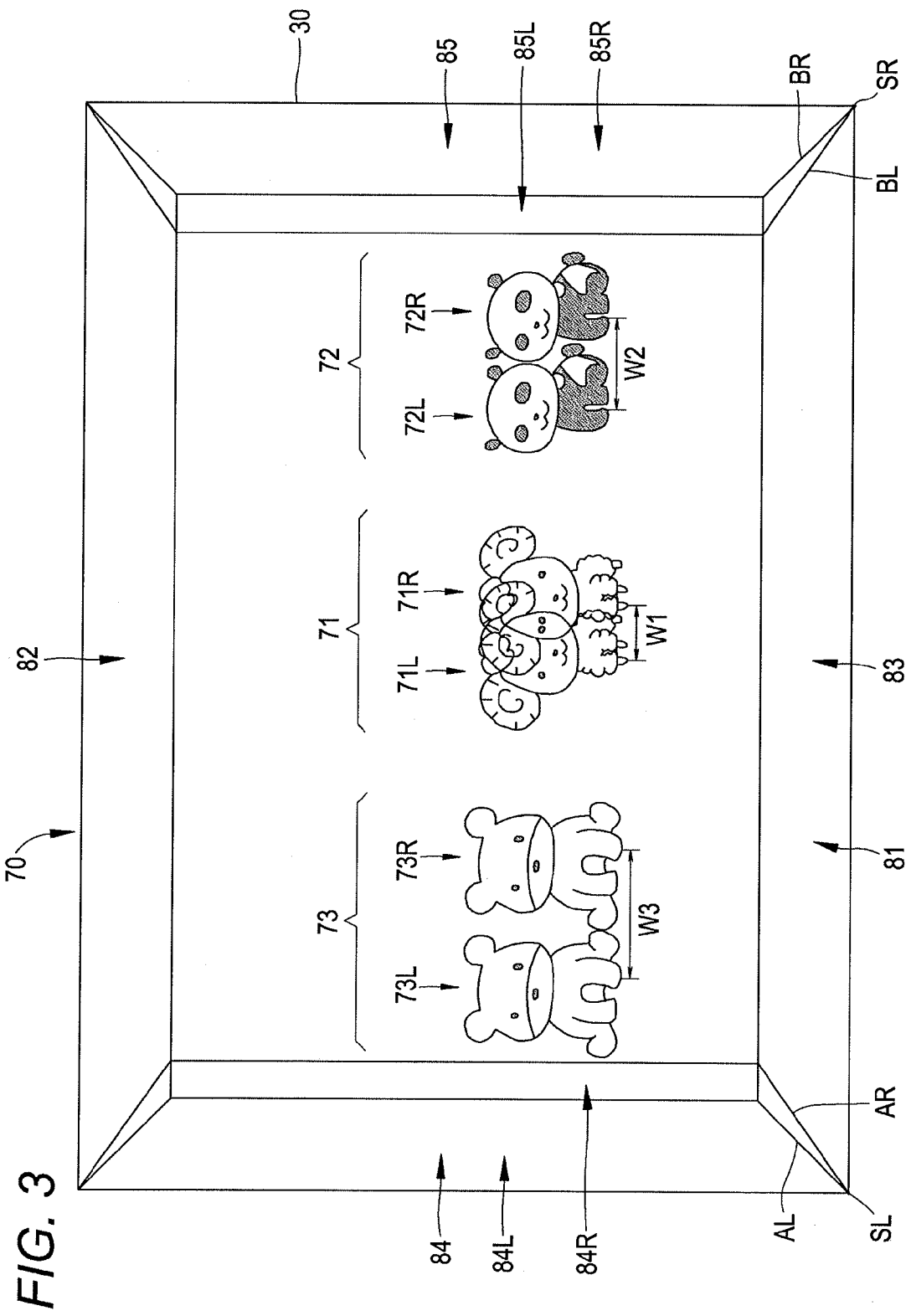
FIG. 3 is a front view illustrating an optotype image serving as a stereoscopic vision test optotype used in the optotype presenting apparatus.
Figure 4:
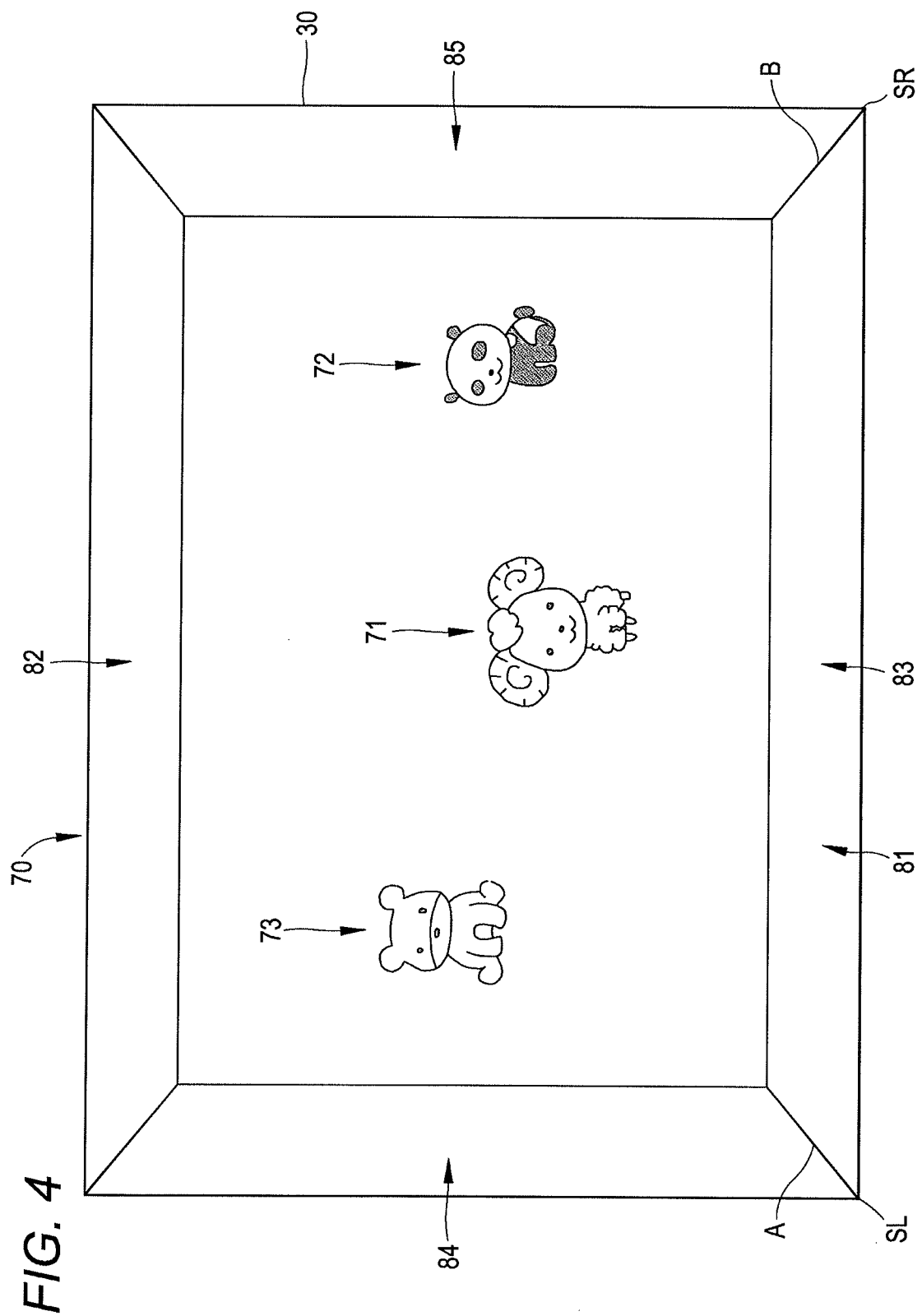
FIG. 4 is a diagram illustrating an optotype to be seen by an examinee in a stereoscopic vision test by the use of the optotype presenting apparatus.

Next, an optotype for a stereoscopic vision test (stereoscopic vision test optotype) to be presented (displayed) on the display 31 is described. FIG. 3 is a front view illustrating an optotype image serving as the stereoscopic vision test optotype according to the embodiment. FIG. 4 is a diagram illustrating an optotype (optotype image) to be seen by an examinee when a stereoscopic vision test is performed by the use of the optotype presenting apparatus 100. That is, this diagram illustrates an optotype (optotype image) seen by normal eyes of an examinee who can see an optotype stereoscopically through the pair of polarized glasses 90 (or phoropter 200). In this embodiment, a test distance from the optotype presentation part 30 (display 31) to eyes of an examinee is 5 meters.

An optotype image 70 is an optotype to be displayed on the display 31, and is displayed across a screen serving as a presentation region of the display 31. The optotype image 70 includes a plurality of optotypes generating different parallaxes for a stereoscopic vision test. The display 31 has a display surface (pixel surface) serving as a reference plane that does not generate a parallax. In the optotype image 70 of this embodiment includes a first object optotype 71, a second object optotype 72, and a third object optotype 73. These test optotypes are seen by an examinee as sinking. In addition, the optotype image 70 includes a frame optotype (frame-shaped optotype) 81 serving as a guide optotype for guiding the examinee to see the test optotype stereoscopically. The frame optotype 81 is seen by the examinee as sinking.

In this embodiment, the optotype image 70 includes an optotype such as an animal character optotype and a landscape optotype for small children (to receive attentions from small children). The object optotypes 71 through 73 that are character optotypes are displayed in positions around a middle portion of the optotype image 70, that is, in positions different from a position of the frame optotype 81.

The object optotype 71 includes an optotype 71L for a left eye and an optotype 71R for a right eye, and theses optotypes 71L and 71R generate a predetermined first parallax. An interval between the optotypes 71L and 72R is W1. The interval refers to an interval between corresponding feature points of right and left optotypes on the display 31. The object optotype 72 includes an optotype 72L for a left eye and an optotype 72R for a right eye, and these optotypes 72L and 72R generate a predetermined second parallax that differs from the first parallax. An interval between the optotypes 72L and 72R is W2. The object optotype 73 includes an optotype 73L for a left eye and an optotype 73R for a right eye, and these optotypes 73L and 73R generate a predetermined third parallax that differs from the first parallax and the second parallax. An interval between the optotypes 73L and 73R is W3. The intervals W1 through W3 correspond to amounts of sinking of the object optotypes 71 through 73, respectively. The interval W3 is wider than the interval W2 so that the object optotype 73 appears to be farther than the object optotype 72. Moreover, the interval W1 is narrower than the interval W2 so that the object optotype 71 appears to be nearer than the object optotype 72. Thus, in this embodiment, the intervals W1 through W3 have the following relationship: interval W1<interval W2<interval W3 (first parallax<second parallax<third parallax). For example, the parallaxes corresponding to the intervals W1, W2, and W3 are 7 arcminutes, 8 arcminutes, and 10 arcminutes, respectively. Thus, a relative difference between the parallax by the object optotype 71 and the parallax by the object optotype 72 is 1 arcminute. Moreover, a relative difference between the parallax by the object optotype 72 and the parallax by the object optotype 73 is 2 arcminutes. Therefore, these parallaxes are used in the stereoscopic test to determine whether an examinee has a stereoscopic vision function that distinguishes the 1 arcminute or the 2 arcminutes. A parallax (interval between object optotypes) can be changed according to a stereoscopic vision function to be tested. Such a change can be made by, for example, editing and/or creating the optotype image 70.

The frame optotype 81 generates a predetermined fourth parallax, so that the frame optotype 81 appears (is seen) to sink relative to a display surface (pixel surface) of the display 31 serving as the reference plane. An amount of sinking of the frame optotype 81 is smaller than that of each of the object optotypes 71 through 73 so that the optotypes 71 through 73 are readily seen stereoscopically. The fourth parallax differs from (smaller than) the first through third parallaxes. The frame optotype 81 is arranged outside the optotype image 70 so as not to disturb visibility of the object optotypes 71 through 73. The frame optotype 81 includes an upper frame optotype 82, a lower frame optotype 83, a left frame optotype 84, and a right frame optotype 85 that are arranged in an outer circumferential portion of the optotype image 70.

The frame optotypes in the right and left sides in the frame optotype 81 generate the fourth parallax (hereinafter called frame parallax). The left frame optotype 84 includes a left frame optotype 84L for a left eye and a left frame optotype 84R for a right eye. The optotypes 84L and 84R generate a predetermined frame parallax. Similarly, the right frame optotype 85 includes a right frame optotype 85L for a left eye and a right frame optotype 85R for a right eye. The optotypes 85L and 85R generate a predetermined frame parallax (substantially the same as the parallax generated by optotypes 84L and 84R).

For example, it is assumed that a line A is a border between the lower frame optotype 83 and the left frame optotype 84 (see FIG. 4). A line AL is a border between the left frame optotype 84L for a left eye and the lower frame optotype 83 (see FIG. 3). The line AL extends toward a center of the screen (optotype image 70) from a point of origin SL located in a lower left corner of the frame optotype 81. A line AR is a border between the left frame optotype 84R for a right eye and the lower frame optotype 83 (see FIG. 3). The line AR extends toward the center of the screen from the point SL. The line AL extends toward outside relative to the line AR. When the lines AR and AL are stereoscopically seen, the line A of FIG. 4 appears to extend toward the center of the screen on the display 31.

In addition, it is assumed that a line B is a border between the lower frame optotype 83 and the right frame optotype 85 (see FIG. 4). A line BL is a border between the right frame optotype 85L for a left eye and the lower frame optotype 83 (see FIG. 3). The line BL extends toward a center of the screen (optotype image 70) from a point of origin SR located in a lower right corner of the frame optotype 81. A line BR is a border between the right frame optotype 85R for a right eye and the lower frame optotype 83 (see FIG. 3). The line BR extends toward the center of the screen (optotype image 70) from the point SR. When the lines BR and BL are stereoscopically seen, the line B of FIG. 4 appears to extend toward the center of the screen on the display 31.

The points of origins SL and SR do not generate a parallax. These points SL and SR are provided on a display surface of the display 31. The directions in which the lines AL and AR extend vary depending on a frame parallax. The distance between lines AL and AR continuously (gradually) widens. Similarly, the directions in which the lines BL and BR extend vary depending on a frame parallax. The distance between the lines BL and BR continuously (gradually) widens. Thus, the lower frame optotype 83 and the left frame optotype 84 appear (are seen) to sink continuously from the point SL. The lower frame optotype 83 and the right frame optotype 85 appear (are seen) to sink continuously from the point SR. In this embodiment, it is assumed that an amount of sinking corresponding to the frame parallax is smaller than amounts of sinking corresponding to the object optotypes 71 through 73. For example, a frame parallax is 3 arcminutes such that the frame optotype 81 appears in front of the object optotype 71. This frame parallax may be any parallax as long as the parallax can guide an examinee to see the object optotypes 71 through 73 stereoscopically. The frame parallax may be a parallax allowing the frame optotype 81 to appear to sink to a position of an optotype (object optotype 71) having a small sinking amount among the object optotypes 71 through 73. Moreover, the frame parallax may be greater than a parallax corresponding to a sinking amount of any of the object optotypes 71 through 73.

A relationship between the upper frame optotype 82 and the left frame optotype 84 is similar to that between the lower frame optotype 83 and the left frame optotype 84. A relationship between the upper frame optotype 82 and the right frame optotype 85 is similar to that between the lower frame optotype 83 and the right frame optotype 85.

Accordingly, the frame optotype 81 appears (is seen) to sink continuously (gradually) from the display surface (a reference plane not generating parallax) of the display 31. That is, the frame optotype 81 generates a parallax such that an examinee can see the frame optotype 81 as floating or sinking continuously from the reference plane. Consequently, when the examinee sees the object optotypes 71 through 73, a peering effect is produced, thereby attracting the examinee to pay attention to around the center portion of the optotype image 70. In addition, since the frame optotype 81 appears to sink continuously (gradually), an examinee who is not accustomed to a stereoscopic vision test can be readily guided to see the object optotypes 71 through 73 stereoscopically. For example, when a line of sight of an examinee is guided to around the center portion of the optotype image 70, the line of sight of the examinee follows a line (e.g., line A, line B) in the corner of the frame optotype 81. This allows the examinee to be gradually accustomed to seeing in a stereoscopic manner, and then the examinee can be guided to see the object optotypes 71 through 73 serving as test optotypes stereoscopically.

A description is given of a stereoscopic vision test that is performed by the use of the optotype presenting apparatus 100 having above structure. An examiner instructs an examinee wearing a pair of the polarized glasses 90 (or examinee having phoropter 200 arranged in front of right and left eyes thereof) to be in a test position that is predetermined distance away (5 meters in this embodiment) from the optotype presenting apparatus 100. Subsequently, the examiner presses the key 61 on the remote control 60 to present the stereoscopic vision test optotype (optotype image) 70 on the optotype presenting apparatus 100. The control unit 40 accesses (retrieves) data of the optotype image 70 stored in the memory 41 based on a command signal from the remote control 60. The control unit 40 allows the optotype image 70 corresponding to the retrieved data to be displayed on the display 31.

The light from the optotypes 71L through 73L for a left eye, the upper frame optotype 82, the lower frame optotype 83, the left frame optotype 84L, and the right frame optotype 85L of the optotype image 70 enters a left eye of the examinee through the optical region 32a and the polarizing filter 90L (or polarizing filter 201L). Similarly, the light from the optotypes 71R through 73R for a right eye, the upper frame optotype 82, the lower frame optotype 83, the left frame optotype 84R, and the right frame optotype 85R enters a right eye of the examinee through the optical region 32b and the polarizing filter 90R (polarizing filter 201R). Therefore, the examinee sees that the frame optotype 81 appears to sink from the display surface of the display 31. In addition, the examinee sees that the object optotypes 71 through 73 appear to sink and to be in back of the frame optotype 81.

Then, the examiner determines how the examinee can see the object optotypes 71 through 73. When the examinee tells that the object optotype 71 appears in front (forward) of the object optotype 72 (object optotype 72 is in back (rearward) of the object optotype 71) and the object optotype 72 appears in front (forward) of the object optotype 73 (the object optotype 73 is in back (rearward) of the object optotype 72), the examiner finds that the examinee has a stereoscopic vision function.

If an examinee cannot see an optotype stereoscopically well (cannot see or perceive optotype), the examiner leads the examinee to pay attention to the corner of the display 31 (points SL and SR of the frame optotype 81 in the outer side in the optotype image 70 on the screen). The examiner also leads the examinee to see the object optotypes 71 through 73 arranged around the center of the optotype image 70 while following the lines A and B of the frame optotype 81 with eyes thereof. The examinee can readily see the object optotypes 71 through 73 arranged around the center of the optotype image 70 in a stereoscopic manner by following the lines A and B of the frame optotype 81 that appear to sink continuously. When such procedure leads the examinee to see the object optotypes 71 through 73 stereoscopically, the stereoscopic vision test can be further proceeded. On the other hand, in a case where an examinee cannot see the object optotypes 71 through 73 stereoscopically even if such procedure is used, the examinee is found to have a stereoscopic vision function problem.

According to the optotype presenting apparatus 100, therefore, a guide optotype is used to guide a line of sight of an examinee to a test optotype, so that the examinee can readily see the test optotype stereoscopically. Such an optotype presenting apparatus 100 can allow an examinee who is not accustomed to the stereoscopic vision test to understand the meaning of the test. Thus, the stereoscopic vision test (binocular vision test) can be efficiently performed.

In addition to the above description, the frame optotype 81 may be an optotype that appears to sink stepwise from a display surface (reference plane) of the display 31. In such a case, the frame optotype 81 generates a parallax so as to be seen by an examinee as sinking or floating stepwise from the reference plane. In such a case, the peering effect also occurs when the examinee sees the object optotypes 71 through 73.

Now, a description is given of a second embodiment that is a modification of the first embodiment. An optotype presenting apparatus according to the second embodiment allows a guide optotype to be presented (displayed) as a moving image, thereby guiding an examinee to see an optotype image stereoscopically. Note that components that are similar to those of the first embodiment are given the same reference numerals as above and description thereof will not be repeated.

Figure 5:
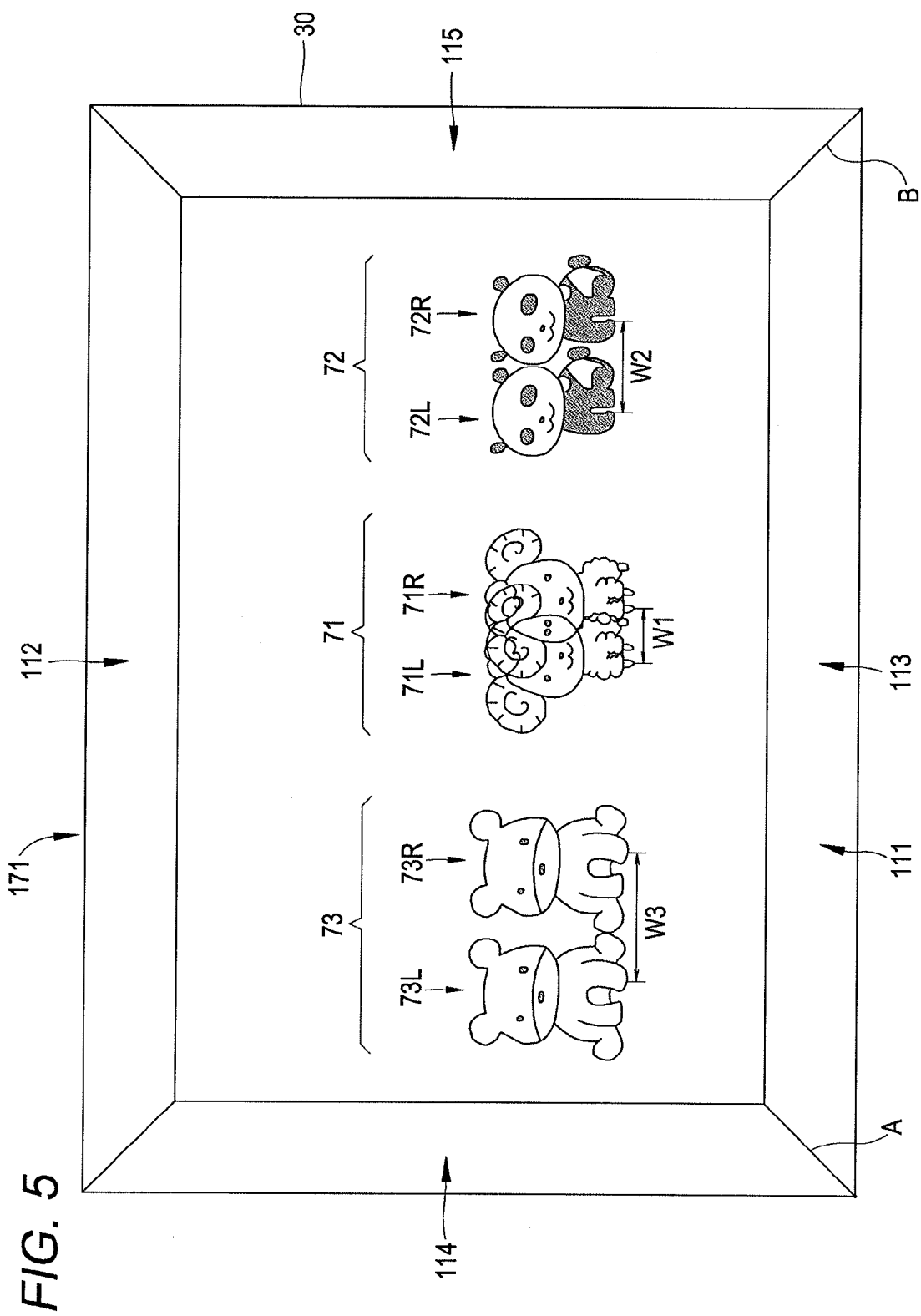
FIG. 5 is a diagram illustrating an initial state of an optotype image serving as a stereoscopic vision test optotype according to a second embodiment.
Figure 6:
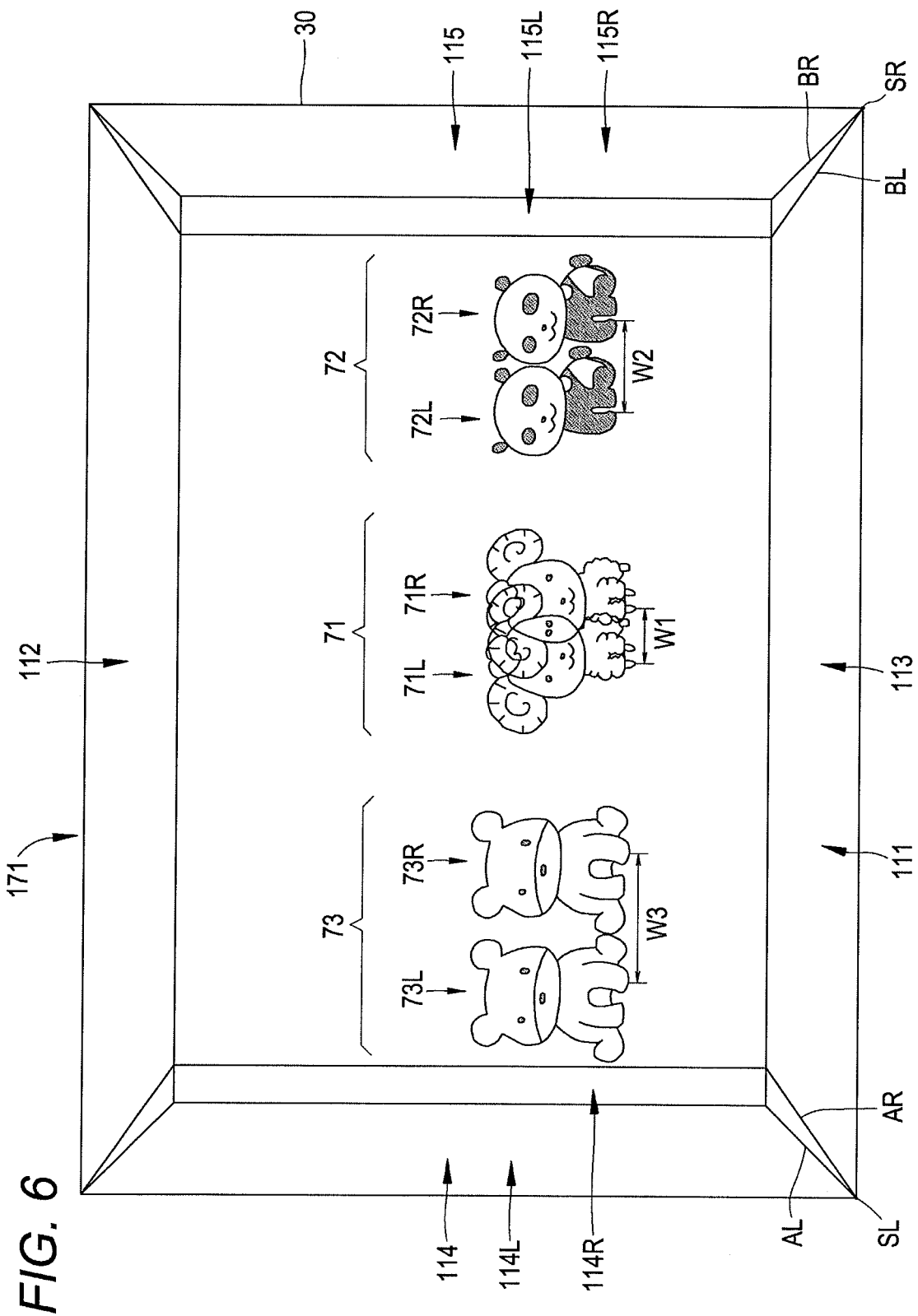
FIG. 6 is a diagram illustrating the optotype image after a certain time period has elapsed from the initial state.

An optotype image 171 of the second embodiment is described by mainly referring to the difference between the optotype image 171 and the optotype image 70 of the first embodiment. FIGS. 5 and 6 are front views illustrating the optotype image 171 serving as an optotype for a stereoscopic vision test according to the second embodiment. FIG. 5 illustrates an initial state of the optotype image 171, and FIG. 6 illustrates the optotype image 171 at the end of moving image playback when a certain time period has elapsed from the initial state of FIG. 5. A control unit 40 performs display of the moving image.

The optotype image 171 includes object optotypes 71 through 73 and a frame optotype 111. The object optotypes 71 through 73 are similar to those of the first embodiment. The object optotypes 71 through 73 have intervals W1 through W3 to generate parallaxes in any state.

The frame optotype 111 includes an upper frame optotype 112, a lower frame optotype 113, a left frame optotype 114, and a right frame optotype 115 that are arranged in an outer circumferential portion of the optotype image 171. In the initial state (FIG. 5), the frame optotype 111 does not generate a parallax. Accordingly, the frame optotype 111 appears to be in a position on a display surface (reference plane) of the display 31 when an examinee sees the frame optotype 111 through a pair of polarized glasses 90 (frame optotype 111 does not appear to sink). In the end state in which the moving image playback is finished (see FIG. 6), on the other hand, the frame optotype 111 generates a frame parallax (predetermined amount of parallax) similar to the frame parallax of the first embodiment (see FIG. 3). The examinee sees the frame optotype 111 illustrated in FIG. 6 stereoscopically with right and left eyes similarly to when seeing the frame optotype 81 illustrated in FIG. 4. The left frame optotype 114 includes a left frame optotype 114L for a left eye and a left frame optotype 114R for a right eye. The right frame optotype 115 includes a right frame optotype 115L for a left eye and a right frame optotype 115R for a right eye.

Upon input of a start signal from a moving image start switch (not shown) arranged on a remote control 60, the control unit 40 controls display on the display 31 such that the frame optotype 111 of the optotype image 171 gradually changes from the initial state illustrated in FIG. 5 to the end state illustrate in FIG. 6. That is, the control unit 40 controls display on the display 31 such that a parallax generated from the frame optotype 111 serving as a guide optotype gradually increases with time (frame optotype 111 gradually sinks). The control unit 40 controls the display 31 such that the change of the parallax stops when a parallax generated from the frame optotype 111 reaches a predetermined amount (when reaching a state of FIG. 6).

Accordingly, the optotypes for a left eye (upper frame optotype 112, lower frame optotype 113, left frame optotype 114L, right frame optotype 115L, line AL, line BL) are displayed as moving images so as to move toward a center of a presentation region. Moreover, the optotypes for a right eye (upper frame optotype 112, lower frame optotype 113, left frame optotype 114R, right frame optotype 115R, line AR, line BR) are displayed as moving images so as to move toward the center of the presentation region. In these moving image displays, the parallax generated from the optotypes for a left eye and the optotypes for a right eye gradually increase with time. As for the examinee who is binocularly seeing these moving images, the lines A and B of FIG. 5 appear to gradually extend from the respective points SL and SR, whereas the frame optotype 111 appears to gradually sink with time. Such moving image displays can guide the examinee to readily see the object optotypes 71 through 73 stereoscopically.

In the moving image display of the frame optotype 111 serving as a guide optotype, the parallax generated from the optotype may have a change rate (speed) with time of "10 arcseconds to 3 arcminutes per second". If the change speed is faster than "3 arcminutes per second", a movement of the guide optotype is too fast to see with right and left eyes, causing reduction in the effect on the moving image display. If the change speed is slower than "10 arcseconds per second", a movement of the guide optotype becomes too slow. The longer the test time, the harder the examinee to pay attention to the guide optotype. In this embodiment, a change speed of the parallax is "30 arcseconds per second", for example.

If the change speed of the parallax is constant, an examinee who is actually seeing a guide optotype in a binocular manner sees that a movement of the guide optotype appears to be faster as a parallax generated from the guide optotype increases. Accordingly, the change speed of the parallax may be reduced as the parallax generated from the guide optotype increases, so that the optotype appears to move at a constant speed for the examinee.

Moreover, in the moving image display of the guide optotype, a moving image may be repeatedly displayed from the initial state illustrated in FIG. 5 to the end state illustrated in FIG. 6 until a predetermined end signal is input. When a moving image of sinking (or floating) of the frame optotype 111 is repeatedly displayed, an examinee is readily guided to see the object optotypes 71 through 73 stereoscopically.

In the moving image display of the guide optotype, operation of the key 61 on the remote control 60 allows a command signal for switching the optotype to be input to the control unit 40. The control unit 40 allows the optotype image 171 to be displayed on the display 31 in response to the command signal. Then, operation of a switch (not shown) arranged on the remote control 60 allows a start signal for starting a moving image display of the guide optotype (frame optotype 111) to be input to the control unit 40. The control unit 40 allows the moving image to be displayed on the display 31 in response to the start signal. Moreover, when the moving image of the guide optotype is set to be repeatedly displayed, such a moving image is repeatedly displayed. In this case, an examiner operates a moving image stop switch (not shown) arranged on the remote control 60 when the display of the moving image needs to be stopped. The operation of the moving image stop switch allows the end signal to be input to the control unit 40. Subsequently, the control unit 40 allows the guide optotype (frame optotype 111) as illustrated in FIG. 6 to be displayed on the display 31 in a fixed manner in response to the end signal.

In the optotype presenting apparatus according to the second embodiment, therefore, the guide optotype is displayed as a moving image, so that a sinking amount of the guide optotype changes (increases) continuously. Such a change leads an examinee who is paying attention to the guide optotype (frame optotype 111) to see the moving image. Herein, the moving image in which a guide optotype in a state of not generating a parallax (guide optotype not need to be seen stereoscopically) appears to sink gradually. The examinee can be gradually accustomed to seeing the optotype stereoscopically by keeping the eyes on the moving image, and then readily guided to see the object optotypes 71 through 73 stereoscopically.

Figure 7:
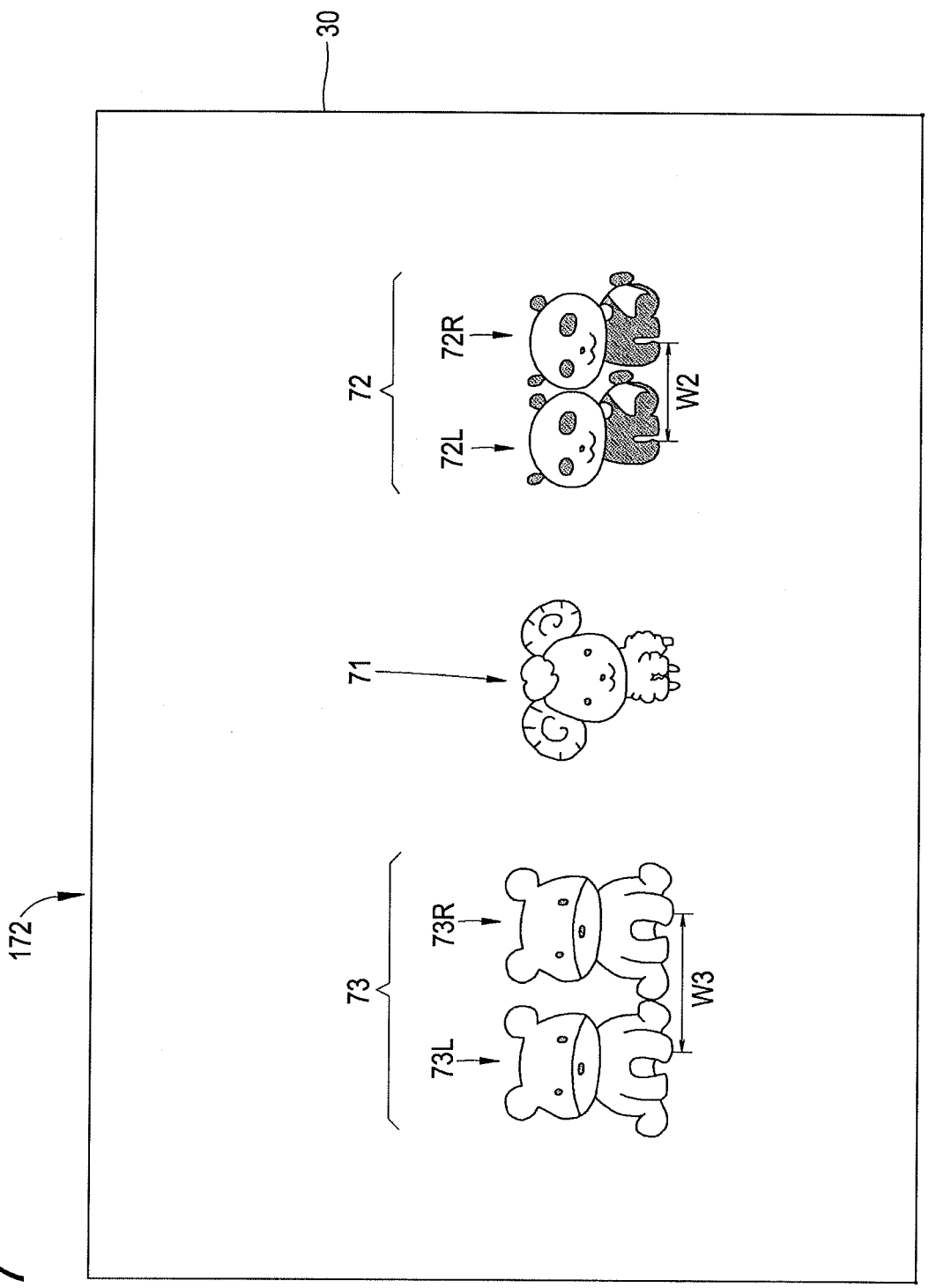
FIG. 7 is a diagram illustrating an initial state of an optotype image serving as a stereoscopic vision test optotype according to a third embodiment.

Next, an optotype presenting apparatus according to a third embodiment is described. This optotype presenting apparatus is a modification of the above configuration that presents the guide optotype as the moving image. FIGS. 7 and 8 are front views illustrating an optotype image 172 serving as a stereoscopic vision test optotype according to the third embodiment. FIG. 7 illustrates an initial state of the optotype image 172, and FIG. 8 illustrates the optotype image 172 at the end of moving image playback when a certain time period has elapsed from the initial state of FIG. 7. A control unit 40 performs display of the moving image. Note that components that are similar to those of the above embodiments are given the same reference numerals as above and description thereof will not be repeated.

The optotype image 172 does not have a frame optotype unlike the above embodiments. In the optotype presenting apparatus of the third embodiment, an object optotype 71 is used as a guide optotype. Object optotypes 72 and 73 are displayed on a display 31 as similar to the above embodiments. As illustrated in FIG. 7, the object optotype 71 is displayed on the display 31 so as not to generate a parallax at the initial state of a moving image display. Then, a parallax generated from an object optotype 71L for a left eye and an object optotype 71R for a right eye changes with time so as to increase gradually. As for an examinee who is binocularly seeing the optotype image 172, the object optotype 71 appears to sink gradually from a reference plane similarly to the second embodiment, thereby readily guiding the examinee to see the object optotypes 72 through 73 stereoscopically. In a state in which the change with time of the parallax generated from the optotypes 71L and 71R has stopped (state illustrated in FIG. 8), the optotype 71 not only serves as the guide optotype, but also serves as a stereoscopic vision test optotype generating a parallax corresponding to a predetermined interval W1. A stereoscopic vision function of the examinee is tested based on whether or not there is a difference in how the optotype 71 and other optotypes for a stereoscopic test, i.e., the optotypes 72 and 73, are seen (whether or not there is a difference in near and far vision).

In the optotype presenting apparatus according to this embodiment, the object optotype 71 also serving as the guide optotype is displayed, whereas the object optotypes 72 and 73 may not be displayed. In such a case, after the moving image playback of the object optotype 71 displayed as the guide optotype is finished, the optotypes 71L and 71R of the object optotype 71 are displayed in a fixed manner with an interval W1 corresponding a predetermined parallax (e.g., 2 arc-minutes), thereby allowing the stereoscopic vision test.

The control unit 40 allows the object optotype 71 being displayed on the display 31 to change from a state of not generating a parallax to a state of generating a parallax based on a moving image start signal input from the remote control 60. According to the third embodiment, display conditions such as a change speed of the parallax generated from the guide optotype and a continuous or stepwise display are substantially similar to those according to the second embodiment.

Therefore, moving image display of an object optotype serving as a test optotype enables an examinee to readily pay attention to the object optotype, so that the examinee can be gradually accustomed to seeing the optotype stereoscopically. In such a case, the stereoscopic vision test is performed while the examinee is being guided to the object optotype stereoscopically (while the examinee is seeing the object optotype 71).

In the above description, the moving image is displayed to and seen by the examinee such that the optotype appears to sink. Alternatively, the optotype may be displayed as a moving image such that the optotype appears to float. Moreover, an optotype displayed in the presentation region may be displayed as a moving image such that the optotype appears to both sink and float.

According to the first and second embodiments, the frame optotype is used as the guide optotype, but is not limited thereto. The guide optotype may be any optotype that appears (is seen) to sink continuously. The guide optotype may be an optotype that is pictured with depth (recalling depth), for example, an object having a stand shape such as a picture frame, a window frame, a door, and a desk, an object having a box shape such as a cage, a road, and a rail track. Moreover, the guide optotype may be an optotype that is drawn to appear to extend toward back, for example, one or more lines and arrows.

In the above description, the guide optotype which appears (is seen) to sink continuously is used. However, the guide optotype is not limited thereto as long as an examinee can be guided to see a test optotype stereoscopically. A guide optotype that appears to sink stepwise may be used. For example, optotypes each having a pictured pole or tree may be arranged on outer right and left sides within an optotype image such that the optotypes appear to extend backward.

In addition, an optotype generating a parallax corresponding to a predetermined step may be displayed so that a guide optotype appears to sink stepwise. Herein, the predetermined step represents a parallax step by which an examinee can see some degree of difference in parallaxes. The parallax step may be, for example, greater than zero arcsecond and less than 30 arcseconds. If the parallax step is greater than 30 arcseconds, an examinee who is not accustomed to seeing an optotype stereoscopically may not be readily guided to see the optotype in a stereoscopic manner. When the guide optotype is displayed as a moving image, a parallax generated by an optotype may change continuously with time, thereby allowing an examinee to see a smooth movement of the optotype. The parallax change may be performed stepwise as described above.

In the above description, moreover, the test optotype and the guide optotype which appear (are seen) to sink are used. Alternatively, a test optotype and a guide optotype that appear to float may be used. In addition, a guide optotype may be arranged around the center of an optotype image.

In the above description, the reference plane of the guide optotype (surface on which point of origin is positioned) is coincident with the display surface of the display 31. Alternatively, the reference plane of the guide optotype may not be coincident with the display surface of the display 31 as long as the guide optotype can guide an examinee to see the test optotype stereoscopically. For example, the reference plane of the guide optotype may appear to sink slightly (parallax within 20 arcseconds) or float slightly (parallax within 20 arcseconds) from the display surface of the display 31.

In the above description, the guide optotype which generates a parallax is used, thereby guiding an examinee to stereoscopically see the test optotype which generates a parallax. Additionally, a guide optotype with the gradation may be used to guide the examinee to see the test optotype stereoscopically.

Moreover, in the above embodiment, the test optotype is a character, but is not limited thereto. For example, a conventional optotype that has been used for a stereoscopic vision test (stick-shaped optotype (rod optotype) extending in vertical direction) may be used.

In the above embodiment, the polarizing optical member 32 and the polarizing filters 90L and 90R (or polarizing filters 201L and 201R) are used as a unit for splitting an optotype to be presented to right and left eyes of an examinee (optotype to be displayed on display 31). Alternatively, the optotype may be split by a splitting unit with circularly polarized light. Moreover, a known splitting unit may be used, for example, a unit for splitting an optotype according to colors (red/green (or blue)), and a unit for splitting an optotype with an electric shutter.

In addition, the optotype image may be stored in the memory 41 as known image data such as raster image data and vector image data.

The optotype image may be displayed within a predetermined region of a screen instead of an entire screen of the display 31. In such a case, this predetermined region serves as a presentation region. A size of the optotype image (image of test optotype and/or guide optotype) may be changed instead of being fixed.

Moreover, an amount of the sinking or floating of a test optotype and a guide optotype may be changed instead of being fixed.

In the above description, the optotype presenting apparatus uses the display as a presentation unit, but is not limited thereto as long as the presentation unit has a presentation region to display an optotype thereon. For example, a presentation unit employing an optotype projecting method (including an optotype projecting method of test distance saving type) may be used for presentation of an optotype in a presentation region such as a screen and an optotype window. In such a case, a polarizing optical member serving as a portion of a splitting unit for splitting an optotype is arranged (attached) in front of an optotype plate (optotype disk) having an optotype pictured (printed) thereon.

The optotype presenting apparatus according the above embodiments may be expressed as first through seventh optotype presenting apparatuses as follows.

The first optotype presenting apparatus for presenting optotypes to right and left eyes of an examinee to test a binocular vision function of the examinee, the first optotype presenting apparatus includes: an optotype presentation part for presenting an optotype in a predetermined presentation region; a splitting unit for splitting the optotype presented on the optotype presentation part into optotypes generating a parallax so as to be presented to right and left eyes of the examinee; and a control unit for allowing the optotype to be presented on the optotype presentation part. The optotype includes a test optotype arranged near a center portion of the presentation region, and a guide optotype arranged in the presentation region so as to appear to sink or float continuously or stepwise from a predetermined reference plane to guide the examinee to see the test optotype stereoscopically.

The second optotype presenting apparatus is provided according to the first optotype presenting apparatus, in which the reference plane corresponds to a surface of the presentation region.

The third optotype presenting apparatus is provided according to the first or second optotype presenting apparatus, in which the guide optotype is arranged in the presentation region such that the guide optotype appears to sink or float continuously or stepwise toward a center portion from an outer circumferential portion of the presentation region.

The fourth optotype presenting apparatus is provided according to the third optotype presenting apparatus, in which the guide optotype is a frame-shaped optotype arranged in the outer circumferential portion of the presentation region.

The fifth optotype presenting apparatus is provided according to any of the first through fourth optotype presenting apparatuses, in which a storage unit for storing the optotype as image data is further included, the optotype presentation part is a display, and the presentation region is a display region for displaying the optotype including the test optotype and the guide optotype therein.

The sixth optotype presenting apparatus includes: an optotype presentation part for presenting an optotype used to test a visual function of an examinee in a predetermined presentation region; a control unit for allowing a test optotype including a stereoscopic vision test optotype to be presented on the optotype presentation part, the stereoscopic vision test optotype generating a parallax so as to be seen by the examinee as floating or sinking from a predetermined reference plane; and an optotype splitting unit for splitting the test optotype presented on the optotype presentation part into an optotype for a left eye and an optotype for a right eye to present the test optotype to right and left eyes of the examinee. The test optotype includes a guide optotype for guiding the examinee to see the stereoscopic vision test optotype stereoscopically and for generating a parallax that is seen by the examinee as floating or sinking from the reference plane and changes continuously or stepwise.

The seventh optotype presenting apparatus for presenting an optotype used to test stereoscopic vision function of the examinee, the seventh optotype presenting apparatus includes: an optotype presentation part including a presentation region for presenting a test optotype thereon; and an optotype splitting unit for splitting the test optotype presented on the presentation region into an optotype for a left eye and an optotype for a right eye. The test optotype includes a stereoscopic vision test optotype that generates a parallax used to test a stereoscopic vision function of the examinee, and a guide optotype for guiding the examinee to see the stereoscopic vision test stereoscopically. The guide optotype generates a parallax so that the guide optotype is seen by the examinee as floating or sinking from a reference plane continuously or stepwise.

According to these optotype presenting apparatuses, an examinee can readily see an optotype stereoscopically, thereby efficiently performing a binocular vision test such as a stereoscopic vision test.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An optotype presenting apparatus for presenting an optotype used to test a visual function of an examinee, the optotype presenting apparatus comprising:
    an optotype presentation part configured to present the optotype in a predetermined presentation region;
    a control unit configured to cause a test optotype to be presented in the optotype presentation part, the test optotype including a stereoscopic vision test optotype configured to generate a parallax so as to be seen by the examinee as floating or sinking from a predetermined reference plane; and
    an optotype splitting unit configured to split the test optotype presented in the optotype presentation part into an optotype for a left eye and an optotype for a right eye to present the test optotype to right and left eyes of the examinee, wherein
    the test optotype further includes a guide optotype configured to guide the examinee to see the stereoscopic vision test optotype stereoscopically,
    the guide optotype is configured to generate a parallax so that the guide optotype is seen by the examinee as floating or sinking from the reference plane continuously or stepwise, and
    the guide optotype in the presentation region is configured to generate the parallax that changes continuously or stepwise toward a position of the stereoscopic vision test optotype arranged in the presentation region.

2. The optotype presenting apparatus according to claim 1, wherein the guide optotype is configured to generate the parallax that changes continuously or stepwise toward the stereoscopic vision test optotype, from an outer circumferential portion toward a center portion of the presentation region.

3. The optotype presenting apparatus according to claim 1, wherein the guide optotype includes a frame-shaped optotype arranged in an outer circumferential portion of the presentation region.

4. The optotype presenting apparatus according to claim 1, wherein the reference plane corresponds to a surface of the presentation region and is not configured to generate a parallax.

5. The optotype presenting apparatus according to claim 1, wherein the position of the stereoscopic vision test optotype differs from a position of the guide optotype and is near a center portion of the presentation region.

6. The optotype presenting apparatus according to claim 1, wherein the optotype presentation part includes a display, and
the control unit is configured to control the display to display the guide optotype on a screen of the display.

7. The optotype presenting apparatus according to claim 6, wherein the control unit is configured to cause a moving image to be displayed on the screen of the display, the moving image allowing the guide optotype to change with time such that the parallax generating by the guide optotype increases gradually.

8. The optotype presenting apparatus according to claim 7, wherein the control unit is configured to control the display such that the parallax stops changing when an amount of the parallax generated by the guide optotype reaches a predetermined amount.

9. The optotype presenting apparatus according to claim 8, wherein the guide optotype is configured to be used as the stereoscopic vision test optotype after the parallax stops changing.

10. An optotype presenting apparatus for presenting an optotype used to test a visual function of an examinee, the optotype presenting apparatus comprising:
an optotype presentation part configured to present the optotype in a predetermined presentation region;
a control unit configured to cause a test optotype to be presented in the optotype presentation part, the test optotype including a stereoscopic vision test optotype configured to generate a parallax so as to be seen by the examinee as floating or sinking from a predetermined reference plane; and
an optotype splitting unit configured to split the test optotype presented in the optotype presentation part into an optotype for a left eye and an optotype for a right eye to present the test optotype to right and left eyes of the examinee, wherein
the test optotype further includes a guide optotype configured to guide the examinee to see the stereoscopic vision test optotype stereoscopically,
the guide optotype is configured to generate a parallax so that the guide optotype is seen by the examinee as floating or sinking from the reference plane continuously or stepwise, and
the guide optotype is a frame-shaped optotype arranged in an outer circumferential portion of the presentation region.

11. An optotype presenting apparatus for presenting an optotype used to test a visual function of an examinee, the optotype presenting apparatus comprising:
an optotype presentation part configured to present the optotype in a predetermined presentation region;
a control unit configured to cause a test optotype to be presented in the optotype presentation part, the test optotype including a stereoscopic vision test optotype configured to generate a parallax so as to be seen by the examinee as floating or sinking from a predetermined reference plane; and
an optotype splitting unit configured to split the test optotype presented in the optotype presentation part into an optotype for a left eye and an optotype for a right eye to present the test optotype to right and left eyes of the examinee, wherein
the test optotype further includes a guide optotype configured to guide the examinee to see the stereoscopic vision test optotype stereoscopically,
the guide optotype is configured to generate a parallax so that the guide optotype is seen by the examinee as floating or sinking from the reference plane continuously or stepwise,
the optotype presentation part includes a display,
the control unit is configured to control the display to display the guide optotype on a screen of the display, and
the control unit is configured to cause a moving image to be displayed on the screen of the display, the moving image allowing the guide optotype to change with time such that the parallax generating by the guide optotype increases gradually.

12. The optotype presenting apparatus according to claim 11, wherein
the control unit is configured to control the display such that the parallax stops changing when an amount of the parallax generated by the guide optotype reaches a predetermined amount.

13. The optotype presenting apparatus according to claim 12, wherein the guide optotype is configured to be used as the stereoscopic vision test optotype after the parallax stops changing.

* * * * *